United States Patent
Albalat et al.

(10) Patent No.: US 9,115,058 B2
(45) Date of Patent: Aug. 25, 2015

(54) PROCESS OF PREPARATION OF OPTICALLY ACTIVE αAMINOACETALS

(75) Inventors: Muriel Albalat, Coudoux (FR); Geraldine Primazot, Compiegne (FR); Didier Wilhelm, Issy les Moulineaux (FR); Jean-Claude Vallejos, La Ciotat (FR)

(73) Assignee: WEYLCHEM LAMOTTE S.A.S., Trusly Breuil (FR)

( * ) Notice: Subject to any disclaimer, the term of this patent is extended or adjusted under 35 U.S.C. 154(b) by 234 days.

(21) Appl. No.: 12/919,247

(22) PCT Filed: Jan. 21, 2009

(86) PCT No.: PCT/EP2009/050665
§ 371 (c)(1),
(2), (4) Date: Aug. 25, 2010

(87) PCT Pub. No.: WO2009/106386
PCT Pub. Date: Sep. 3, 2009

(65) Prior Publication Data
US 2011/0034726 A1   Feb. 10, 2011

(30) Foreign Application Priority Data
Feb. 27, 2008 (FR) .................... 08 01081

(51) Int. Cl.
| C07B 57/00 | (2006.01) |
| C07C 213/00 | (2006.01) |
| C07C 233/47 | (2006.01) |
| C07C 213/10 | (2006.01) |
| C07C 217/40 | (2006.01) |
| C07C 217/48 | (2006.01) |

(52) U.S. Cl.
CPC ............ *C07C 233/47* (2013.01); *C07C 213/10* (2013.01); *C07C 217/40* (2013.01); *C07C 217/48* (2013.01); *C07B 2200/07* (2013.01)

(58) Field of Classification Search
CPC ............................. C07B 57/00; C07C 213/00
USPC .................... 548/400; 564/304, 346
See application file for complete search history.

(56) References Cited

U.S. PATENT DOCUMENTS

| 4,769,486 A | 9/1988 | Harada et al. |
| 5,476,964 A | 12/1995 | House |
| 6,670,486 B1 | 12/2003 | Bakonyl et al. |
| 6,867,284 B1 * | 3/2005 | Matassa et al. ............ 530/329 |
| 7,220,883 B2 | 5/2007 | Serradeil Albalat et al. |
| 2010/0152490 A1 | 6/2010 | Albalat et al. |

FOREIGN PATENT DOCUMENTS

| EP | 0249349 | 12/1987 |
| EP | 0291234 | 11/1988 |
| EP | 0367242 | 5/1990 |
| EP | 0374647 | * 6/1990 |
| EP | 0779261 | 6/1997 |
| EP | 1527041 | 5/2004 |
| FR | 2843112 | 2/2004 |
| JP | 59 170058 | 9/1984 |
| WO | WO96/14857 | 5/1996 |
| WO | WO98/22496 | 5/1998 |
| WO | WO2004/013081 | 2/2004 |

OTHER PUBLICATIONS

International Search Report for PCT/EP2008/056219, dated Jul. 28, 2008.
Translation of Written Opinion of the Internatonal Searching Authority for PCT/EP2008/056219, dated Jul. 28, 2008.
International Search Report for PCT/EP2009/050665, dated Mar. 10, 2009.
Translation of International Preliminary Report on Patentability for PCT/EP2009/050665, dated Mar. 26, 2010.
English Abstract for JP 59 170058, Sep. 29, 1984.
English Abstract for EP 0374647, Jun. 27, 1990.
Tetrahedron (1974), 30(23/24), 4233-4237.
Guillaumie, et al., "Solid—phase synthesis of C—terminal peptide aldehydes from amino acetals anchored to a backbone amide linker (BAL) handle", Tetrahedron Lett., 2000, 41(32), 6131-6135.
Kurt Kahr, et al., "Katalytische Oxydation von primaren Am inen zu Oximen mit Wasserstoffperoxyd", Chemische Berichte., vol. 93, No. 1960, 1960, pp. 132-136.
J. Jurczak et al., Chem. Rev., (1989), 89 (1), 149-164.
M.T. Reetz, Angew Chem., Int. Ed. Engl., (1991), 30 (12), 1531-1546.
D. Enders et al., Angew. Chem., Int. Ed. Engl., (1993), 32 (3), pp. 418-421.
Chemical Abstracts, Heterocyclic Compounds, (1962), 3425.
J. Chem. Soc., 1957, 2146-2158.
J. Med. Chem., 1987, 30(1), 150-156.
J. Org. Chem., 1981, 46(8), 1575-1585.
Bioorg. & Med. Chem. Lett., 2002, 12(4), 701-704.
J. Heterocycl. Chem., 1978, 15(4), 665-670.

* cited by examiner

*Primary Examiner* — Mark Shibuya
*Assistant Examiner* — Sonya Wright
(74) *Attorney, Agent, or Firm* — Michael W. Ferrell

(57) ABSTRACT

The invention relates to a process for preparing optically active α-aminoacetals by resolution of a racemic mixture or of a mixture of enantiomers via the formation of diastereoisomeric salts, and also novel intermediates in the form of diastereoisomeric salts.

20 Claims, No Drawings

PROCESS OF PREPARATION OF OPTICALLY ACTIVE α-AMINOACETALS

The invention relates to a process for preparing optically active α-aminoacetals, and also novel intermediates in the form of diastereoisomeric salts useful for this purpose.

More particularly, the invention relates to a process for resolving a racemic mixture or a mixture of enantiomers by the formation of diastereoisomeric salts, which makes it possible to access the two enantiomers with high optical purities.

Optically active α-aminoacetals are compounds that are particularly advantageous as direct precursors of optically active α-aminoaldehydes.

N-protected α-aminoaldehydes are commonly used as chiral reactants in the total synthesis of biologically active products, as described, for example, in J. Jurczak et al., Chem. Rev., (1989), 89 (1), 149-164 or M. T. Reetz, Angew Chem., Int. Ed. Engl., (1991), 30 (12), 1531-1546, but are not readily commercially available.

The synthetic pathways most commonly described for the preparation of α-aminoacetals use N-protected α-amino acids as reactants, in order to access N-protected α-aminoaldehydes and then α-aminoacetals, either by intermediate formation of a Weinreb amide, or by partial reduction to aldehyde, or by total reduction to α-aminoalcohols and partial reoxidation to N-protected α-aminoaldehydes. These methods for preparing optically active α-aminoacetals have various drawbacks, among which mention may be made of reaction conditions which are restricting for industrial exploitation, or the use of expensive reactants. The main restriction of these syntheses is the limited availability of the starting reactants, namely the natural α-amino acids.

Other methods have been used, such as the asymmetric reduction of optically active imines, derived from α-keto acetals, as described, for example, in application EP 374647, which are difficult to access, with the exception of pyruvaldehyde dimethylacetal.

Finally, methods using a chiral inductor have been developed in order to access these optically active α-aminoacetals from dialkoxyethanals, such as the methodology using the chiral auxiliaries SAMP, (S)-1-amino-2-(methoxymethyl) pyrrolidine, and RAMP, (R)-1-amino-2-(methoxymethyl) pyrrolidine, as described, for example, in D. Enders et al., Angew. Chem., Int. Ed. Engl., (1993), 32 (3), 418-21, or aminotriazoles, (S,S)-4-amino-3,5-bis(1-hydroxyethyl)-1,2,4-triazole, as described, for example, in application EP1527041. Nevertheless, these various syntheses use either reactants that are expensive or difficult to prepare, or synthesis, purification or optical enrichment steps which are restricting from the industrial point of view.

The technical problem to be solved therefore consists in providing a process for preparing optically active α-aminoacetals which makes it possible to solve the abovementioned problems while starting from commercially available and inexpensive materials.

The invention therefore relates to a process for preparing optically active α-aminoacetals of formula (R)-(I) or (S)-(I)

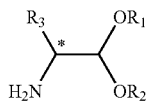
(R)-(I) or (S)-(I)

in which:

$R_1$ and $R_2$, which may be identical or different, represent a linear or branched $C_1$-$C_{12}$ alkyl group, or else $R_1$ and $R_2$ are joined so as to form a 1,3-dioxolan-2-yl group which is unsubstituted or substituted on positions 4 and/or 5 with one or more linear or branched $C_1$-$C_6$ alkyl substituents, or a 1,3-dioxan-2-yl group which is unsubstituted or substituted on positions 4 and/or 5 and/or 6 with one or more linear or branched $C_1$-$C_6$ alkyl substituents;

$R_3$ represents a linear or branched $C_1$-$C_{12}$ alkyl group; a $C_2$-$C_{12}$ alkenyl group; a $C_2$-$C_{12}$ alkynyl group; a $C_3$-$C_{10}$ cycloalkyl group; a $C_3$-$C_{10}$ cycloalkenyl group; a cycloalkylalkyl group in which the cycloalkyl and alkyl groups are as defined above; a heterocycloalkyl group containing 3 to 10 atoms; a heterocycloalkylalkyl group in which the heterocycloalkyl and alkyl groups are as defined above; a monocyclic, bicyclic or tricyclic $C_6$-$C_{14}$ aryl group; a heteroaryl group containing 5 to 14 atoms; an arylalkyl group or a heteroarylalkyl group, in which the aryl, heteroaryl and alkyl groups are as defined above; a C(=O)$R_4$ group in which $R_4$ represents a linear or branched $C_1$-$C_{12}$ alkyl group, a cycloalkyl group, a cycloalkenyl group, a heterocycloalkyl group, an aryl group or a heteroaryl group, as defined above, or an $OR_5$ group in which $R_5$ represents an H, a linear or branched $C_1$-$C_{12}$ alkyl group, a $C_3$-$C_{10}$ cycloalkyl group, a $C_3$-$C_{10}$ cycloalkenyl group, a heterocycloalkyl group, an aryl group or a heteroaryl group, as defined above, or $R_4$ represents an $NHR_6$ group in which $R_6$ represents an H, a linear or branched $C_1$-$C_{12}$ alkyl group, a $C_3$-$C_{10}$ cycloalkyl group, a $C_3$-$C_{10}$ cycloalkenyl group, a heterocycloalkyl group, an aryl group or a heteroaryl group, as defined above; all the alkyl, alkenyl, alkynyl, cycloalkyl, cycloalkenyl, cycloalkylalkyl, heterocycloalkyl, heterocycloalkylalkyl, aryl, heteroaryl, arylalkyl and heteroarylalkyl radicals above being unsubstituted or substituted;

the asterisk * signifies that the C atom is an asymmetrical carbon, which process comprises the resolution of a compound of formula (I) in racemic form or in the form of mixtures of enantiomers

(I)

in which $R_1$, $R_2$, $R_3$ and the asterisk * are as defined above, with a resolving agent, characterized in that said process comprises the steps consisting in:

a) reacting a compound of formula (I) with an optically active α-amino acid represented by general formulae (II) to (VI)

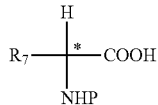
(II)

-continued

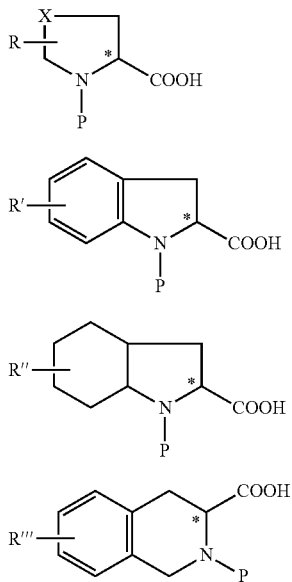

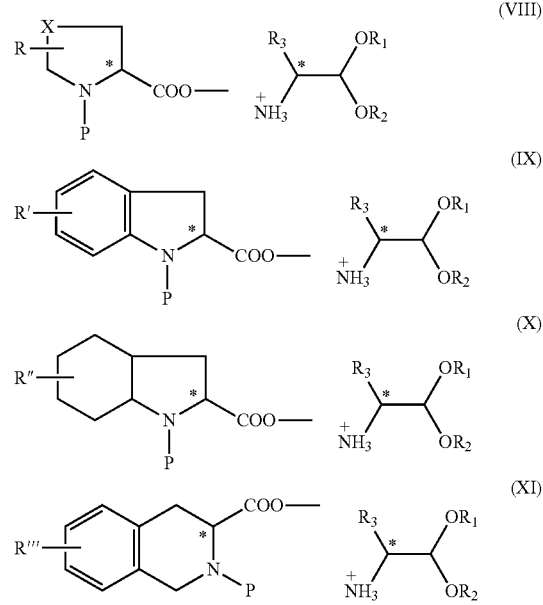

in which:

R₇ represents a linear or branched $C_1$-$C_{12}$ alkyl group; a $C_3$-$C_{10}$ cycloalkyl group; a cycloalkylalkyl group in which the cycloalkyl and alkyl groups are as defined above; a monocyclic, bicyclic or tricyclic $C_6$-$C_{14}$ aryl group; an arylalkyl group in which the alkyl and aryl groups are as defined above; a heteroaryl group containing 5 to 14 atoms; or a heteroarylalkyl group in which the alkyl and heteroaryl groups are as defined above; all the alkyl, cycloalkyl, aryl, arylalkyl, heteroaryl and heteroarylalkyl radicals being unsubstituted or substituted;

P represents a 9-fluorenylmethoxycarbonyl protective group; a —COR₈ group in which R₈ represents hydrogen, a linear or branched $C_1$-$C_6$ alkyl group, a monocyclic, bicyclic or tricyclic $C_6$-$C_{14}$ aryl group or an OR₉ group in which R₉ represents a linear or branched $C_1$-$C_6$ alkyl group or an arylalkyl group in which the aryl and alkyl groups are as defined above; or an —S(C₂)R₁₀ group in which R₁₀ represents a linear or branched $C_1$-$C_6$ alkyl group, a monocyclic, bicyclic or tricyclic $C_6$-$C_{14}$ aryl group or an arylalkyl group in which the aryl and alkyl groups are as defined above; all the 9-fluorenylmethoxycarbonyl, alkyl, aryl and arylalkyl groups being unsubstituted or substituted;

X represents a carbon or sulphur atom;

R, R', R'' and R''', independently of one another, represent one or more hydrogen atom(s), halogen atom(s) or hydroxyl group(s) or an oxo (=O) group;

the asterisk * signifies that the C atom is an asymmetrical carbon, in a solvent, so as to form diastereoisomeric salts represented by formulae (VII) to (XI):

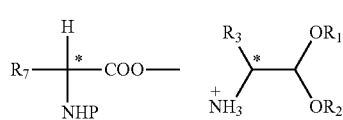

in which R₁, R₂, R₃, R₇, P, X, R, R', R'', R''' and the asterisk * are as defined above, b) separating the diastereoisomeric salts of formulae (VII) to (XI) formed in the medium, and c) releasing the optically active α-aminoacetal of formula (R)-(I) or (S)-(I).

The expression "optically active" is intended to mean that the compound of formula (R)-(I) or (S)-(I) possesses an enantiomeric excess, relative to the other enantiomer, within the range of from 1% to 100%, preferably within the range of from 50% to 100%, and more preferably within the range of from 70% to 100%.

The term "enantiomeric excess" is intended to mean the ratio of the excess of the desired enantiomer relative to the undesired enantiomer.

This ratio is calculated according to one of the following equations:

$$\% \, ee\cdot(R) = ([R]-[S]/[R]+[S]) \times 100\%$$

$$ee\cdot(S) = ([S]-[R]/[R]+[S]) \times 100$$

in which:

% ee·(R) represents the enantiomeric excess of R isomer

% ee·(S) represents the enantiomeric excess of S isomer

[R] represents the concentration of R isomer, and

[S] represents the concentration of S isomer.

The term "releasing" is intended to mean that the optically active α-aminoacetal is no longer in the form of diastereoisomeric salts of formulae (VII) to (XI).

According to one preferred aspect of the invention, use will be made of a compound of formula (I) in racemic form or in the form of mixtures of enantiomers, in which R₁ and R₂, which may be identical or different, represent a linear or branched $C_1$-$C_6$ alkyl group, in particular methyl or ethyl;

R₃ represents a group chosen from a substituted or unsubstituted, linear or branched $C_1$-$C_6$ alkyl group; a substituted or unsubstituted monocyclic, bicyclic or tricyclic $C_6$-$C_{14}$ aryl group, preferably phenyl; a substituted or unsubstituted arylalkyl group in which the aryl and alkyl groups are as defined above, preferably benzyl, or phenylethyl; a substituted or unsubstituted cycloalkyl group, preferably cyclohexyl; and a substituted or unsubstituted cycloalkylalkyl group in which the cycloalkyl and alkyl groups are as defined above.

Optional substituents of the $R_3$, $R_4$, $R_5$ and $R_6$ groups may be independently chosen from the following groups: halogen, OH (optionally protected, for example in the form of an ether with tetrahydropyran or in the form of an ester with the acetyl group), $NH_2$, $CC_2H$, $SC_3H$, $CF_3$, alkoxycarbonyl (or alkyl-O—CO—), amide, alkyl-N—CO—, alkylenedioxy (or —O-alkylene-O—), alkylsulphonyl (or alkyl-$SC_2$—), alkylsulphonylcarbamoyl (or alkyl$SC_2$—NH—C(=O)—), —O-cycloalkyl, acyloxy, acylamino, alkylamino, dialkylamino, arylamino, diarylamino, arylalkylamino, oxo protected in the form of a cyclic or noncyclic ketal, formyl protected in the form of a cyclic or noncyclic acetal, aryloxy, alkyl, cycloalkyl, aryl, arylalkyl, heteroaryl and alkoxy.

According to another preferred aspect of the process according to the invention, a compound of formula (I) in racemic form or in the form of mixtures of enantiomers is reacted with an optically active α-amino acid represented by general formula (II) or (III)

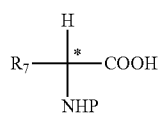

(II)

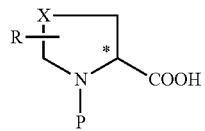

(III)

in which:
R₇ represents a linear or branched $C_1$-$C_6$ alkyl group which is unsubstituted or substituted with one or more hydroxyl, —NHP', —C(O)NH₂, —NH—C(=NH)—NHP', —SH, —S—CH₃, —CC₂H or phenyl groups, in which P' represents hydrogen or an acetyl, propionyl, formyl, tosyl, benzoyl, ethoxycarbonyl, tert-butoxycarbonyl, benzyloxycarbonyl or 9-fluorenylmethoxycarbonyl group; a cyclohexyl group; a phenyl group; a benzyl or naphthyl group which is unsubstituted or substituted one or more times with a halogen atom, a hydroxyl group, an NO₂ group, a phenyl group or a $C_1$-$C_3$ alkoxy group; a pyridyl group; an imidazolylmethyl group; a pyridylmethyl group; or a thiazolylmethyl or indolylmethyl group;

P represents an acetyl, propionyl, formyl, tosyl, benzoyl, ethoxycarbonyl, tert-butoxycarbonyl, benzyloxycarbonyl or 9-fluorenylmethoxycarbonyl group;

X represents a carbon atom;

R represents a hydrogen atom.

In the products of formulae (I), (S)-(I), (R)-(I) and (II) to (XI), and also for the substituents, the groups indicated have the meanings which follow:

the halogen group denotes fluorine, chlorine, bromine or iodine atoms;

the linear or branched $C_1$-$C_{12}$ alkyl group denotes, for example, methyl, ethyl, propyl, isopropyl, butyl, isobutyl, sec-butyl, tert-butyl, pentyl, isopentyl, sec-pentyl, tert-pentyl, neopentyl, hexyl, isohexyl, sec-hexyl, tert-hexyl, heptyl, octyl, nonyl, decyl, undecyl or dodecyl groups, linear or branched $C_1$-$C_6$ alkyl groups being preferred;

the linear or branched $C_2$-$C_{12}$ alkenyl group denotes, for example, ethenyl or vinyl, propenyl or allyl, 1-propenyl, n-butenyl, i-butenyl, 3-methylbut-2-enyl, n-pentenyl, hexenyl, heptenyl, octenyl or decenyl groups, linear or branched $C_2$-$C_4$ alkenyl groups being preferred;

the linear or branched $C_2$-$C_{12}$ alkynyl group denotes, for example, ethynyl, propynyl or propargyl, butynyl, n-butynyl, i-butynyl, 3-methylbut-2-ynyl, pentynyl or hexynyl groups, linear or branched $C_2$-$C_4$ alkynyl groups being preferred;

the linear or branched $C_1$-$C_{12}$ alkoxy group denotes, for example, methoxy, ethoxy, propoxy, isopropoxy, linear, secondary or tertiary butoxy, pentoxy, hexoxy or heptoxy groups, linear or branched $C_1$-$C_6$ alkoxy groups being preferred;

the cycloalkyl group denotes a monocyclic or bicyclic $C_3$-$C_{10}$ carbocyclic group, such as cyclopropyl, cyclobutyl, cyclopentyl or cyclohexyl groups;

the cycloalkenyl group denotes a monocyclic or bicyclic $C_3$-$C_{10}$ carbocyclic group containing at least one double bond, such as cyclobutenyl, cyclopentenyl or cyclohexenyl groups;

the cycloalkylalkyl group denotes a group in which the cycloalkyl and alkyl residues have the meanings mentioned above, such as cyclopropylmethyl, cyclobutylmethyl, cyclopentylmethyl, cyclohexylmethyl, cycloheptylmethyl, cyclopropylethyl or cyclohexylethyl groups;

the aryl group denotes a monocyclic, bicyclic or tricyclic $C_6$-$C_{14}$ carbocyclic aromatic group, such as phenyl, naphthyl, indenyl or anthracenyl groups, and more particularly the phenyl group;

the arylalkyl group denotes a group in which the aryl and alkyl residues have the meanings mentioned above, such as benzyl, phenylethyl, 2-phenylethyl or naphthylmethyl groups;

the heterocycloalkyl group denotes a monocyclic or bicyclic carbocyclic group containing 3 to 10 atoms, interrupted with one or more heteroatoms, which may be identical or different, chosen from oxygen, nitrogen or sulphur atoms, such as the dioxolanyl, dioxanyl, dithiolanyl, thioxolanyl, oxiranyl, piperazinyl, piperidinyl, pyrrolidinyl, imidazolidinyl, pyrazolidinyl, morpholinyl, tetrahydrofuryl, tetrahydrothienyl or thiazolidinyl group;

the heterocycloalkylalkyl group denotes a group in which the heterocycloalkyl and alkyl residues have the meanings mentioned above;

the heteroaryl group denotes a monocyclic, bicyclic or tricyclic, aromatic or partially unsaturated carbocyclic group interrupted with one or more heteroatoms, which may be identical or different, chosen from oxygen, nitrogen or sulphur atoms, containing 5 to 14 atoms, such as furyl (2-furyl, for example), thienyl (2-thienyl, 3-thienyl, for example), pyrrolyl, diazolyl, thiazolyl, isothiazolyl, oxazolyl, oxadiazolyl, 3- or 4-isoxazolyl, imidazolyl, pyrazolyl, isoxazolyl, pyridyl (2- or 3- or 4-pyridyl, for example), pyrimidinyl, pyridizinyl, pyrazinyl, tetrazolyl, benzothienyl (3-benzothienyl, for example), benzofuranyl, indolyl, purinyl, quinolyl, isoquinolyl, chromanyl or naphthyridinyl groups;

the heteroarylalkyl group denotes a group in which the heteroaryl and alkyl residues have the meanings mentioned above;

the alkyl-O—CO— group denotes a linear or branched $C_2$-$C_{12}$ group in which the alkyl group has the meaning indicated above;

the alkylene group denotes a divalent, linear or branched $C_1$-$C_6$ hydrocarbon-based group, such as methylene, ethylene, propylene or isopropylene;

the —O-alkylene-O— group denotes a linear or branched $C_1$-$C_6$ group in which the alkylene group has the meaning indicated above;

the alkyl-$SC_2$— group denotes a linear or branched $C_1$-$C_{12}$ group in which the alkyl group has the meaning indicated above;

the alkylsulphonylcarbamoyl group denotes a linear or branched $C_2$-$C_{12}$ group in which the alkyl group has the meaning indicated above;

the —O-cycloalkyl group denotes a group in which the cycloalkyl group has the meaning indicated above;

the acyloxy group denotes an r-CO—O— group in which r represents an alkyl, cycloalkyl, heterocycloalkyl, aryl or heteroaryl group, these groups having the values indicated above, such as acetoxy or propionyloxy;

the acylamino group denotes an r-CO—N— group in which r has the meaning indicated above, such as acetamido;

the alkyl-N—CO— group denotes a group in which the alkyl group has the meaning indicated above;

the alkylamino, dialkylamino, arylamino, diarylamino, and arylalkylamino groups denote groups in which the alkyl and aryl groups have the meanings indicated above;

the aryloxy group denotes an aryl-O— group in which the aryl group has the meaning indicated above, such as phenoxy or naphthyloxy.

As optically active α-amino acid, use will, for example, be made of an α-amino acid chosen from N-acetyl-(L)-phenylalanine, N-acetyl-(D)-phenylalanine, N-acetyl-(L)-leucine, N-acetyl-(D)-leucine, N-acetyl-(L)-valine, N-acetyl-(D)-valine, N-acetyl-(L)-tyrosine, N-acetyl-(D)-tyrosine, N-acetyl-(L)-methionine, N-acetyl-(D)-methionine, N-acetyl-(L)-asparagine, N-acetyl-(D)-asparagine, N-tosyl-(L)-phenylalanine, N-tosyl-(D)-phenylalanine, N-ethoxycarbonyl-(L)-phenylglycine and N-ethoxycarbonyl-(D)-phenylglycine.

N-Acetyl-(L)-phenylalanine or N-acetyl-(D)-phenylalanine are optically active α-amino acids which are preferred for the purposes of the invention.

The racemic α-aminoacetals used for the resolution in the process of the invention can be prepared by adaptation of methods described in the literature, for example starting from α-halogenated acetals followed by amination, as described, by way of indication, in Heterocyclic Compounds, (1962), 3425, J. Chem. Soc., 1957, 2146-2158, J. Med. Chem., 1987, 30(1), 150-156 and J. Org. Chem., 1981, 46(8), 1575-1585. They can also be obtained starting from α-amino acids and then by formation of a Weinreb amide, reduction and acetalization as described in Bioorg. & Med. Chem. Lett., 2002, 12(4), 701-704 and WO 9822496.

FR 2843112 describes the addition of organometallic compounds to aminotriazole derivatives for obtaining racemic α-aminoacetals or mixtures of enantiomers.

The reduction of oxime derivatives of α-keto acetals described in J. Heterocycl. Chem., 1978, 15(4), 665-670 and EP 367242 also makes it possible to obtain racemic α-aminoacetals.

In step a) of the process according to the invention, preferred implementation conditions are the following:

the optically active α-amino acid is present in a molar ratio of between 0.1 and 1 molar equivalent, relative to the compound of formula (I), preferably 0.5 molar equivalent;

the solvent is chosen from the group comprising isopropanol, ethanol, water, acetone, methyl isobutyl ketone, tetrahydrofuran, acetonitrile, ethyl acetate, toluene and methyl tert-butyl ether, and mixtures thereof;

the concentration of the compound of formula (I) is between 1% and 40% by weight, preferably between 3% and 9% by weight;

the reaction temperature is between 0° C. and 120° C., preferably between 5° C. and the boiling point of the reaction medium, in particular with temperature holds or gradients being performed during heating and cooling;

the duration of the reaction is between 30 min and 48 h.

At the end of step a), the resolution is carried out by selective crystallization of the diastereoisomeric salts of formulae (VII) to (XI).

This is because, advantageously, during the reaction of step a), one of the two diastereoisomeric salts preferentially precipitates. The separation of the least soluble diastereoisomeric salt from the reaction medium is preferably performed by filtration during step b).

During step c), the optically active α-aminoacetal is obtained by treatment of the separated diastereoisomeric salt with an alkaline aqueous solution such as sodium hydroxide or potassium hydroxide, or an acidic aqueous solution such as hydrochloric acid. Preferably, treatment with a dilute aqueous solution of sodium hydroxide is used, optionally followed by extraction with an appropriate organic solvent for releasing the desired optically active α-aminoacetal. Neutralization of the alkaline solution makes it possible to recycle the optically active α-amino acid.

In preferred conditions for implementing the process according to the invention, it is possible, before releasing the optically active α-aminoacetal of formula (R)-(I) or (S)-(I) as defined above, to subject the diastereoisomeric salts of formulae (VII) to (XI) obtained after step b) to at least one recrystallization or reslurrying step, in particular for improving the optical purity (ee≥95%).

According to one of its subsequent aspects, the invention therefore relates to a process for preparing optically active α-aminoacetals of formula (R)-(I) or (S)-(I) as defined above, in which the diastereoisomeric salts of formulae (VII) to (XI) obtained after step b) are subjected to at least one recrystallization or reslurrying step.

The recrystallization or the reslurrying may, for example, be carried out in an inert solvent or in a mixture of inert solvents, for instance isopropanol, ethanol, acetone, water, tetrahydrofuran, acetonitrile, ethyl acetate, methyl tert-butyl ether (MTBE), methyl isobutyl ketone (MIBK) or toluene, at a temperature of between 0° C. and 120° C., preferably between ambient temperature and the boiling point of the reaction medium, in particular by optionally performing temperature holds or gradients during heating and cooling, for a period of between 30 min and 48 h. The dilution of the medium is generally between 1% and 20% by mass relative to the unit of mass of the salt to be recrystallized or reslurried, preferably between 3% and 9% by mass.

The reaction medium solution recovered after separation of the least soluble diastereoisomeric salt can be treated so as to obtain a mixture enriched in the enantiomer having the configuration opposite to that of the enantiomer obtained from the least soluble diastereoisomeric salt.

According to one of its subsequent aspects, the invention therefore relates to a process for preparing optically active α-aminoacetals of formula (R)-(I) or (S)-(I) as defined above, comprising the steps consisting in:

recovering, from the reaction medium, a diastereoisomeric salt represented by general formulae (VI) to (XI), as defined above, which was not separated during step b), and releasing the optically active α-aminoacetal of formula (R)-(I) or (S)-(I).

Said diastereoisomeric salt may, for example, be recovered by concentration to dryness, and the release of the optically active α-aminoacetal may be carried out, for example, by treatment with an alkaline aqueous solution, optionally followed by extraction with a suitable organic solvent, as described above for step c) of the process according to the invention.

A subject of the present invention is also novel intermediates for preparing an optically active α-aminoacetal of formula (R)-(I) or (S)-(I), i.e. the diastereoisomeric salts of formulae (VII) to (XI) as defined above.

Among these, the diastereoisomeric salts of formula (VII) or (VIII) below

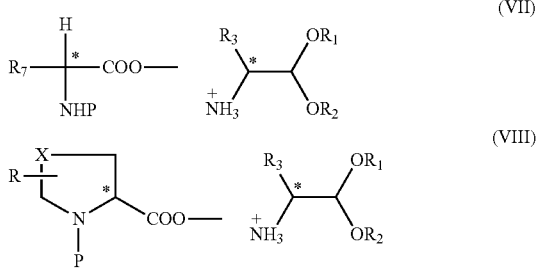

in which:
R$_7$ represents a linear or branched C$_1$-C$_6$ alkyl group which is unsubstituted or substituted with one or more hydroxyl, —NHP', —C(O)NH$_2$, —NH—C(=NH)—NHP', —SH, —S—CH$_3$, —CC$_2$H or phenyl groups, in which P' represents hydrogen or an acetyl, propionyl, formyl, tosyl, benzoyl, ethoxycarbonyl, tert-butoxycarbonyl, benzyloxycarbonyl or 9-fluorenylmethoxycarbonyl group; a cyclohexyl group; a phenyl group; a benzyl or naphthyl group which is unsubstituted or substituted one or more times with a halogen atom, a hydroxyl group, an NO$_2$ group, a phenyl group or a C$_1$-C$_3$ alkoxy group; a pyridyl group; an imidazolylmethyl group; a pyridylmethyl group; or a thiazolylmethyl or indolylmethyl group;

P represents an acetyl, propionyl, formyl, tosyl, benzoyl, ethoxycarbonyl, tert-butoxycarbonyl, benzyloxycarbonyl or 9-fluorenylmethoxycarbonyl group;

X represents a carbon atom;

R represents a hydrogen atom, are preferred compounds.

Particularly preferred diastereoisomeric salts may be chosen from the following compounds:
(R)-1-benzyl-2,2-dimethoxyethylammonium N-acetyl-(L)-phenylalaninate,
(S)-1-benzyl-2,2-dimethoxyethylammonium N-acetyl-(D)-phenylalaninate,
(R)-1-isobutyl-2,2-dimethoxyethylammonium N-acetyl-(L)-phenylalaninate,
(S)-1-isobutyl-2,2-dimethoxyethylammonium N-acetyl-(D)-phenylalaninate,
(S)-1-phenyl-2,2-dimethoxyethylammonium N-acetyl-(L)-phenylalaninate,
(R)-1-phenyl-2,2-dimethoxyethylammonium N-acetyl-(D)-phenylalaninate,
(R)-1-(4-methylbenzyl)-2,2-dimethoxyethylammonium N-acetyl-(L)-phenylalaninate,
(S)-1-(4-methylbenzyl)-2,2-dimethoxyethylammonium N-acetyl-(D)-phenylalaninate, and
(S)-1-(2-phenylethyl)-2,2-dimethoxyethylammonium N-acetyl-(L)-phenylalaninate.

The following examples illustrate the invention in a non-limiting manner.

In the examples, the optical purity of the (R)- or (S)-α-aminoacetals is determined by chiral HPLC, either directly on the compounds of formula (I), or on derivatives, preferably on the carbamate derivatives in which the amine function is protected with a benzyloxycarbonyl (—C(O)—O-Bz) group.

The optical purity is measured by the enantiomeric exess, ee, the value of which is given by the equation mentioned above.

EXAMPLE 1

Resolution of Racemic 1-benzyl-2,2-dimethoxyethylamine with N-acetyl-(L)-phenyl-alanine 1) Preparation of (R)-1-benzyl-2,2-dimethoxyethylammonium N-acetyl-(L)-phenyl-alaninate (Compound of Formula (VII)—R$_1$=R$_2$=Methyl, R$_3$=R$_7$=Benzyl, P=Acetyl)

In a 250 ml three-necked flask equipped with a mechanical stirrer, a condenser and a thermometer, 6 g (30.8 mmol, 1 mol·eq.) of racemic 1-benzyl-2,2-dimethoxyethylamine and 3.18 g (15.4 mmol, 0.5 mol·eq.) of N-acetyl-(L)-phenylalanine (Sigma Aldrich) are introduced into 94 g of isopropanol (solution at 6%). The medium is stirred and heated at 50° C. for 3 h, and then a temperature hold is performed at 40° C. for 2 h. At the end of this hold, the temperature is returned slowly to ambient temperature and stirring is continued overnight at this temperature.

The precipitate is filtered off under vacuum and the solid is washed with cyclohexane (approximately 100 ml) (filtrate 1), and then oven-dried at 40° C. under vacuum. A mass of 3 g of (R)-1-benzyl-2,2-dimethoxyethylammonium N-acetyl-(L)-phenylalaninate is obtained in the form of a white solid, i.e. a yield of 50% relative to the N-acetyl-(L)-phenylalanine.

Molecular formula: $C_{22}H_{30}N_2O_5$

Molar mass: 402.49 g·mol$^{-1}$

NMR (200 MHz/DMSO-d$^6$):

$^1$H NMR: δ 1.78 (s, 3H, CH$_3$); 2.63-2.74 and 3.05-3.14 (syst. AB, 2H, CH$_2$); 2.79-2.92 (m, 2H, CH$_2$); 3.2-3.4 (m, 1H, CH); 3.33 (s, 3H, CH$_3$), 3.38 (s, 3H, CH$_3$), 4.2 (d, J=4.8 Hz, 1H, CH), 4.32 (m, 1H, CH); 5.11 (broad s, NH$_3^+$); 7.1-7.4 (m, 10H, H$_{aromatic}$) and 7.86 (d, 1H, NH) ppm.

$^{13}$C NMR: δ 22.56 (CH$_3$); 36.06 (CH$_2$); 37.31 (CH$_2$); 53.36 (CH); 54.51 (CH); 54.85 (CH$_3$); 55.12 (CH$_3$); 105.25 (CH), 125.95-126.23-127.88-128.27-129.16-129.29 (CH$_{aromatic}$); 137.96-138.59 (C$_{aromatic}$), 168.66 (C=O) and 173.71 (C=O) ppm.

Melting point: Mp=159° C.

Optical rotation: α$^{25}_D$=+42.2° (MeOH, c=1)

2) Preparation of the (R) and (S) enantiomers of 1-benzyl-2,2-dimethoxyethylamine (Compound of Formula (R)-(I) or (S)-(I)—R$_1$=R$_2$=Methyl, R$_3$=Benzyl)

The salt is taken up in 53 g of isopropanol (solution at 5.5%) and the medium is heated at 50° C. for approximately 1 h 30. The temperature is allowed to return to ambient temperature slowly, and the medium is kept at this temperature overnight with stirring. After filtration, the solid is washed with 50 ml of cyclohexane and oven-dried at 40° C.

The salt is treated with an aqueous solution of sodium hydroxide and the aqueous phase is extracted with CH$_2$Cl$_2$. After concentration of the solvent, a mass of 1.23 g of (R)-1-benzyl-2,2-dimethoxyethylamine is obtained, i.e. a yield of 41% relative to the N-acetyl-(L)-phenylalanine, with an optical purity equal to: ee$_{(R)}$=97% (determined by chiral HPLC).

Filtrate 1 is concentrated and the solid residue is taken up, with stirring, in approximately 100 ml of cyclohexane, filtered under vacuum and washed with 60 ml of cyclohexane. After drying and treatment with an aqueous solution of sodium hydroxide, 1.29 g of optically active (S)-1-benzyl-2,2-dimethoxyethylamine are obtained with an optical purity ee$_{(S)}$=74% (determined by chiral HPLC), i.e. a yield of 43% relative to the N-acetyl-(L)-phenylalanine.

1-benzyl-2,2-dimethoxyethylamine (Colourless Oil)
  Molecular formula: C$_{11}$H$_{17}$NO$_2$
  Molar mass: 195.26 g·mol$^{-1}$
  Boiling point: Bp=115-120° C. under 5 mmHg
  EI MS m/z (% relative intensity): 164 (M-31, 11); 120 (M-75, 96); 104 (M-91, 39); 91 (62); 75 (100).
  NMR (200 MHz/CDCl$_3$):
  $^1$H NMR: δ1.3 (s, 2H, NH$_2$); 2.5 (dd, 1H, syst AB CH$_2$); 3 (dd, 1H, syst AB CH$_2$); 3.15 (m, 1H, CH); 3.49 (s, 6H, CH$_3$); 4.14 (d, J=5.6 Hz, 1H, CH) and 7.19-7.4 (m, 6H, CH$_{aromatic}$) ppm.
  $^{13}$C NMR: δ 38.7 (CH$_2$); 54.2 (CH); 55.05 and 55.19 (CH$_3$); 107.9 (CH); 126.3-128.3-128.56-129.1-129.4 (CH$_{aromatic}$) and 139.1 (C$_{aromatic}$) ppm.
  Chiral HPLC analyses (Chiralcel OD-H, hexane/isopropanol 90/10, 1 ml/min, detection UV 254 nm and polarimeter):
  (S)-(-) enantiomer t$_R$=5.6 min
  (R)-(+) enantiomer t$_R$=6.5 min
  Optical rotation:
  (S)-(-) enantiomer: α$^{25}{}_D$=-27.7° (MeOH, c=1)
  (R)-(+) enantiomer: α$^{25}{}_D$=+ 27.6° (MeOH, c=1)

EXAMPLE 2

Resolution of Racemic 1-benzyl-2,2-dimethoxyethylamine with N-acetyl-(D)-phenylalanine In a 250 ml three-necked flask equipped with a mechanical stirrer, a condenser and a thermometer, 6 g (30.8 mmol, 1 mol·eq.) of racemic 1-benzyl-2,2-dimethoxyethylamine and 3.18 g (15.4 mmol, 0.5 mol·eq.) of N-acetyl-(D)-phenylalanine (Sigma Aldrich) are introduced into 94 g of isopropanol (solution at 6%). The medium is stirred and heated at 50° C. for 3 h, and then a temperature hold is performed at 40° C. for 2 h. At the end of this hold, the temperature is allowed to return to ambient temperature slowly and stirring is continued overnight at this temperature.

The precipitate is filtered off under vacuum and the solid is washed with 100 ml of cyclohexane (filtrate 1), and then oven-dried at 40° C. under vacuum. A mass of 3.85 g of (S)-1-benzyl-2,2-dimethoxyethylammonium N-acetyl-(D)-phenylalaninate is obtained, i.e. a yield of 62% relative to the N-acetyl-(D)-phenylalanine.

The solid is taken up in 66 g of isopropanol (solution at 5.5%) and the medium is heated at 50° C. for approximately 1 h 30. The temperature is allowed to return to ambient temperature slowly and the medium is maintained at this temperature overnight with stirring. After filtration, the solid is washed with 50 ml of cyclohexane and oven-dried at 40° C.

The solid is treated with an aqueous solution of sodium hydroxide and the aqueous phase is extracted with CH$_2$Cl$_2$. After concentration of the solvent, 1.32 g of (S)-1-benzyl-2,2-dimethoxyethylamine are obtained, i.e. a yield of 44% relative to the N-acetyl-(D)-phenylalanine, with an optical purity equal to: ee$_{(S)}$≥99% (determined by chiral HPLC).

The filtrate 1 is concentrated and the solid residue is stirred in approximately 100 ml of cyclohexane, filtered under vacuum and washed with 60 ml of cyclohexane. After drying, the precipitate (1 g, i.e. a yield of 35% relative to the N-acetyl-(D)-phenylalanine) is taken up in 37 g of isoPrOH (5.5% dilution) and the medium is kept stirring for 1 h 30. After filtration, drying of the solid and basic treatment, 0.66 g of optically active (R)-1-benzyl-2,2-dimethoxyethylamine is obtained with an optical purity equal to: ee$_{(R)}$=91% (determined by chiral HPLC), i.e. a yield of 22% relative to the N-acetyl-(D)-phenylalanine.

(S)-1-benzyl-2,2-dimethoxyethylammonium N-acetyl-(D)-phenylalaninate (White Solid)

(Compound of Formula (VII)—R$_1$=R$_2$=Methyl, R$_3$=R$_7$=Benzyl, P=Acetyl)
  Molecular formula: C$_{22}$H$_{30}$N$_2$O$_5$
  Molar mass: 402.49 g·mol$^{-1}$
  NMR (200 MHz/DMSO-d$^6$):
  $^1$H NMR: δ 1.78 (s, 3H, CH$_3$); 2.63-2.74 and 3.05-3.14 (syst. AB, 2H, CH$_2$); 2.79-2.92 (m, 2H, CH$_2$); 3.2-3.4 (m, 1H, CH); 3.33 (s, 3H, CH$_3$), 3.38 (s, 3H, CH$_3$), 4.2 (d, J=4.8 Hz, 1H, CH), 4.32 (m, 1H, CH); 5.11 (broad s, NH$_3{}^+$); 7.1-7.4 (m, 10H, H$_{aromatic}$) and 7.86 (d, 1H, NH) ppm.
  $^{13}$C NMR: δ 22.56 (CH$_3$); 36.06 (CH$_2$); 37.31 (CH$_2$); 53.36 (CH); 54.51 (CH); 54.85 (CH$_3$); 55.12 (CH$_3$); 105.25 (CH), 125.95-126.23-127.88-128.27-129.16-129.29 (CH$_{aromatic}$); 137.96-138.59 (C$_{aromatic}$), 168.66 (C=O) and 173.71 (C=O) ppm.
  Melting point: Mp=159° C.
  Optical rotation: α$^{25}{}_D$=-39.6° (MeOH, c=1)

EXAMPLE 3

Preparation of compounds of formula (R)-(I) or (S)-(I) in which:
  R$_1$=R$_2$=methyl
  R$_3$=isobutyl, phenyl, 4-methylbenzyl or Ph-CH$_2$—CH$_2$ The operating conditions of example 1 or 2 are repeated, using N-acetyl-(L)- or -(D)-phenylalanine as resolving agent, various solvents or solvent mixtures, various concentrations by mass of product of formula (I), various temperature conditions and various reaction durations, and performing one or more recrystallizations of the precipitated salts formed, from isopropanol, with various concentrations by mass.

The results obtained are reported in table 1 below.

The solid is treated with an aqueous solution of sodium hydroxide and the aqueous phase is extracted with dichloromethane. After concentration of the organic phase, the (S)-

TABLE 1

| $R_3$ | resolving agent | solvent (concentration by mass) | conditions | Number of recrystallizations (concentration by mass) | ee (%)[a] | yield/resolving agent (%) |
|---|---|---|---|---|---|---|
| isoBu | (L) 0.5 mol. eq. | acetone/isoPrOH 87/13 (6%) | (I) 50° C. 3 h (II) Ta[c] | 2 (7%) | 96 (R)[b] | 50-55 |
| isoBu | (D) 0.5 mol. eq. | acetone/isoPrOH 87/13 (9%) | (I) 50° C. 3 h (II) Ta | 2 (7%) | 96 (S)[b] | 50 |
| Ph | (L) 0.5 mol. eq. | isoPrOH (6%) | (I) 50° C. 3 h (II) Ta | 2 (3%) | 98 (S) | 56 |
| Ph | (D) 0.5 mol. eq. | isoPrOH (6%) | (I) 50° C. 3 h (II) Ta | 2 (5.5%) | 97 (R) | 70-75 |
| 4-MeBn | (L) 0.5 mol. eq. | isoPrOH (9%) | (I) 50° C. 3 h (II) Ta | 2 (5.5%) | 99 (R) | 65 |
| 4-MeBn | (D) 0.5 mol. eq. | isoPrOH (9%) | (I) 50° C. 3 h (II) Ta | 1 (5.5%) | 98 (S) | 68 |
| $PhCH_2CH_2$ | (L) 0.5 mol. eq. | isoPrOH (6%) | (I) 28° C. 2 h (II) 50° C. (III) 30° C. | 2 (3%) | 96 (S) | 19 |
| $PhCH_2CH_2$ | (D) 0.5 mol. eq. | isoPrOH (6%) | (I) 19° C. 2 h (II) 50° C. (III) 30° C. | 2 (3%) | 96 (R) | 23 |

[a]determined by chiral HPLC
[b]determined by chiral HPLC on the carbamate derivatives of N-Cbz type
[c]Ta = ambient temperature The results show that, under all the operating conditions used, an optical purity of greater than or equal to 96% is obtained.

EXAMPLE 4

Resolution of Racemic 1-benzyl-2,2-dimethoxyethylamine with N-acetyl-(L)-leucine In a 100 ml two-necked flask equipped with a magnetic stirrer, a condenser and a thermometer, 1 g (5.1 mmol, 1 eq·mol.) of racemic 1-benzyl-2,2-dimethoxyethylamine is introduced into a 6% solution of N-acetyl-(L)-leucine (Sigma Aldrich) in iso-PrOH (2.5 mmol, 0.5 eq·mol.). The medium is stirred at ambient temperature overnight.

The precipitate obtained is filtered off under vacuum and the solid is washed with 10 ml of cyclohexane, and then oven-dried at 40° C. under vacuum.

The solid is treated with an aqueous solution of sodium hydroxide and the aqueous phase is extracted with dichloromethane. After concentration of the organic phase, 0.14 g of (R)-1-benzyl-2,2-dimethoxyethylamine is obtained, i.e. a yield of 28% relative to the N-acetyl-(L)-leucine, with an optical purity equal to: $ee_{(R)}=83\%$ (determined by chiral HPLC).

EXAMPLE 5

Resolution of Racemic 1-benzyl-2,2-dimethoxyethylamine with N-acetyl-(L)-methionine In a small flask, 0.13 g (0.6 mmol, 1 eq·mol.) of racemic 1-benzyl-2,2-dimethoxyethylamine and 0.06 g (0.3 mmol, 0.5 eq·mol.) of N-acetyl-(L)-methionine are introduced into 1 g of iso-PrOH (11% solution). The flask is subjected to orbital shaking at ambient temperature overnight.

The medium is filtered and the solid is washed with cyclohexane, and then oven-dried at 40° C. under vacuum.

1-benzyl-2,2-dimethoxyethylamine is obtained with an optical purity equal to: $ee_{(S)}=70\%$ (determined by chiral HPLC).

EXAMPLE 6

Resolution of Racemic 1-benzyl-2,2-dimethoxyethylamine with N-tosyl-(L)-phenylalanine In a small flask, 0.1 g (0.5 mmol, 1 eq·mol.) of racemic 1-benzyl-2,2-dimethoxyethylamine and 0.08 g (0.25 mmol, 0.5 eq·mol.) of N-tosyl-(L)-phenylalanine are introduced into 0.15 g of MTBE (approximately 30% solution). The flask is subjected to orbital shaking overnight at ambient temperature.

The medium is filtered and the solid is washed with cyclohexane, and then oven-dried at 40° C. under vacuum.

The solid is treated with an aqueous solution of sodium hydroxide and the aqueous phase is extracted with dichloromethane. After concentration of the organic phase, the (R)-1-benzyl-2,2-dimethoxyethylamine is obtained with an optical purity equal to: $ee_{(R)}=50\%$ (determined by chiral HPLC).

EXAMPLE 7

Resolution of Racemic 1-isobutyl-2,2-dimethoxyethylamine with N-ethoxycarbonyl-(D)-phenylglycine In a 50 ml round-bottomed flask equipped with a magnetic stirrer, a condenser and a thermometer, 0.26 g (1.6 mmol, 1 eq·mol.) of racemic 1-isobutyl-2,2-dimethoxyethylamine is introduced into a solution of 0.18 g (0.8 mmol, 0.5 eq·mol.) of N-ethoxycarbonyl-(D)-phenylglycine in 0.6 g of a mixture of MTBE/EtOH solvents (76/24, approximately 25% solution). The medium is kept stirring at ambient temperature overnight.

The medium is filtered and the solid is washed with cyclohexane, and then oven-dried at 40° C. under vacuum.

The solid is treated with an aqueous solution of sodium hydroxide and the aqueous phase is extracted with dichloromethane. After concentration of the organic phase, the (R)-1-isobutyl-2,2-dimethoxyethylamine is obtained with an optical purity equal to: $ee_{(R)}=39\%$ (determined by chiral HPLC after formation of the N-Cbz-type carbamate derivative).

EXAMPLE 8

Resolution of Racemic 1-(2-phenylethyl)-2,2-diethoxyethylamine with N-acetyl-(L)-phenylalanine In a 50 ml three-necked flask equipped with a mechanical stirrer, a condenser and a thermometer, 0.22 g (0.93 mmol, 1 eq·mol.) of 1-(2-phenylethyl)-2,2-diethoxyethylamine and 0.1 g (0.46 mol, 0.5 eq·mol.) of N-acetyl-(L)-phenylalanine are introduced into 3.45 g of iso-PrOH (6% solution). The medium is stirred for 2 h at ambient temperature and then brought to 50° C., and the return to ambient temperature is carried out slowly. The stirring is maintained overnight.

The medium is filtered and the solid is washed with cyclohexane, and then oven-dried at 40° C. under vacuum.

The solid is treated with an aqueous solution of sodium hydroxide and the aqueous phase is extracted with dichloromethane. After concentration of the organic phase, 0.19 g of 1-(2-phenylethyl)-2,2-diethoxyethylamine (colourless oil) is obtained with an enantiomeric excess of 28% (determined by chiral HPLC).

The invention claimed is:

1. A process for preparing optically active α-aminoacetals of formula (R)-(I) or (S)-(I)

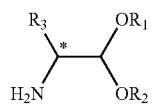

(R)-(I) or (S)-(I)

wherein
$R_1$ and $R_2$, may be identical or different, and are a linear or branched $C_1$-$C_{12}$ alkyl group, or else $R_1$ and $R_2$ are joined so as to form a 1,3-dioxolan-2-yl group wherein the 1,3-dioxolan-2-yl group is unsubstituted or substituted on positions 4 and/or 5 with one or more linear or branched $C_1$-$C_6$ alkyl substituents, or wherein the 1,3-dioxan-2-yl group is unsubstituted or substituted on positions 4 and/or 5 and/or 6 with at least one linear or branched $C_1$-$C_6$ alkyl substituent;
$R_3$ is a linear or branched $C_1$-$C_{12}$ alkyl group; a $C_2$-$C_{12}$ alkenyl group; a $C_2$-$C_{12}$ alkynyl group; a $C_3$-$C_{10}$ cycloalkyl group; a $C_3$-$C_{10}$ cycloalkenyl group; a cycloalkylalkyl group wherein the cycloalkyl and alkyl groups are as defined above; a heterocycloalkyl group containing 3 to 10 atoms; a heterocycloalkylalkyl group wherein the heterocycloalkyl and alkyl groups are as defined above; a monocyclic, bicyclic or tricyclic $C_6$-$C_{14}$ aryl group; a heteroaryl group containing 5 to 14 atoms; an arylalkyl group or a heteroarylalkyl group, in which the aryl, heteroaryl and alkyl groups are as defined above; a $C(=O)R_4$ group wherein $R_4$ is a linear or branched $C_1$-$C_{12}$ alkyl group, a cycloalkyl group, a cycloalkenyl group, a heterocycloalkyl group, an aryl group or a heteroaryl group, as defined above, or an $OR_5$ group wherein $R_5$ is an H, a linear or branched $C_1$-$C_{12}$ alkyl group, a $C_3$-$C_{10}$ cycloalkyl group, a $C_3$-$C_{10}$ cycloalkenyl group, a heterocycloalkyl group, an aryl group or a heteroaryl group, as defined above, or $R_4$ is an $NHR_6$ group wherein $R_6$ is a H, a linear or branched $C_1$-$C_{12}$ alkyl group, a $C_3$-$C_{10}$ cycloalkyl group, a $C_3$-$C_{10}$ cycloalkenyl group, a heterocycloalkyl group, an aryl group or a heteroaryl group, as defined above; all the alkyl, alkenyl, alkynyl, cycloalkyl, cycloalkenyl, cycloalkylalkyl, heterocycloalkyl, heterocyclo-alkylalkyl, aryl, heteroaryl, arylalkyl and heteroarylalkyl radicals above being unsubstituted or substituted;
the asterisk * signifies that the C atom is an asymmetrical carbon,
wherein the process comprises the resolution of a compound of formula (I) in racemic form or in the form of mixtures of enantiomers

(I)

wherein $R_1$, $R_2$, $R_3$ and the asterisk * are as defined above, with a resolving agent,
wherein the process comprises the steps of
a) reacting a compound of formula (I) with an optically active α-amino acid represented by general formulae (II) to (VI)

(II)

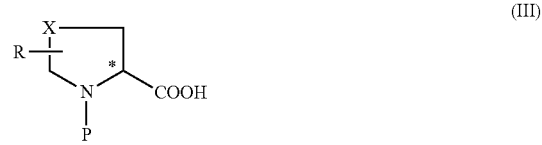

(III)

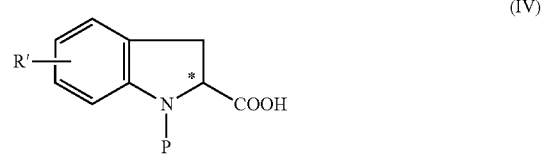

(IV)

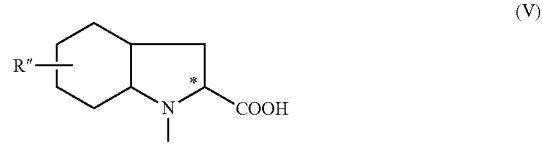

(V)

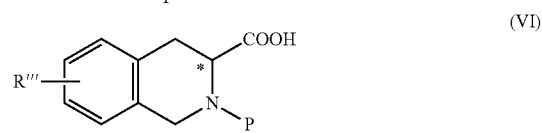

(VI)

wherein
$R_7$ is a linear or branched $C_1$-$C_{12}$ alkyl group; a $C_3$-$C_{10}$ cycloalkyl group; a cycloalkylalkyl group wherein the cycloalkyl and alkyl groups are as defined above; a monocyclic, bicyclic or tricyclic $C_6$-$C_{14}$ aryl group; an arylalkyl group wherein the alkyl and aryl groups are as defined above; a heteroaryl group containing 5 to 14 atoms; or a heteroarylalkyl group wherein the alkyl and heteroaryl groups are as defined above; all the alkyl, cycloalkyl, aryl, arylalkyl, heteroaryl and heteroarylalkyl radicals being unsubstituted or substituted;

P is a 9-fluorenylmethoxycarbonyl protective group; a —$COR_8$ group wherein $R_8$ is a hydrogen, a linear or branched $C_1$-$C_6$ alkyl group, a monocyclic, bicyclic or tricyclic $C_6$-$C_{14}$ aryl group or an $OR_9$ group wherein $R_9$ is a linear or branched $C_1$-$C_6$ alkyl group or an arylalkyl group wherein the aryl and alkyl groups are as defined above; or an —$S(O_2)R_{10}$ group wherein $R_{10}$ is a linear or branched $C_1$-$C_6$ alkyl group, a monocyclic, bicyclic or tricyclic $C_6$-$C_{14}$ aryl group or an arylalkyl group wherein the aryl and alkyl groups are as defined above; all the 9-fluorenylmethoxycarbonyl, alkyl, aryl and arylalkyl groups being unsubstituted or substituted;

X is a carbon or sulphur atom;

R, R', R" and R"', independently of one another, are at least one hydrogen atom, halogen atom or hydroxyl group or an oxo (=O) group;

the asterisk * signifies that the C atom is an asymmetrical carbon, in a solvent, so as to form diastereoisomeric salts represented by formulae (VII) to (XI):

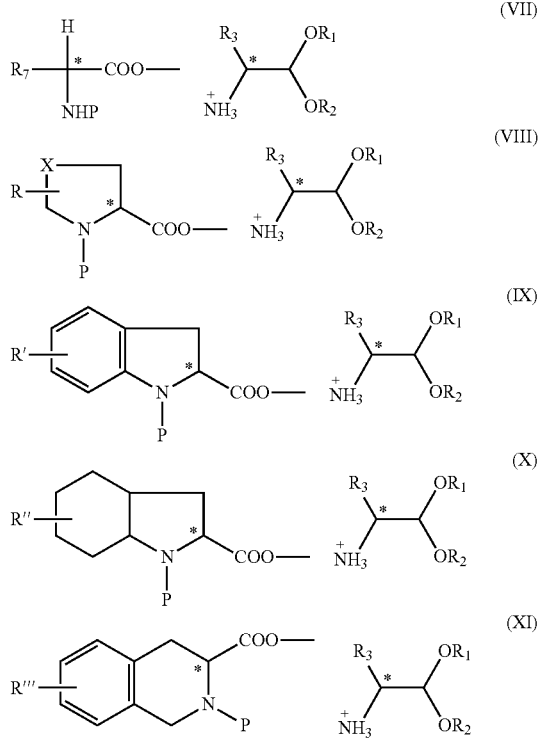

wherein $R_1$, $R_2$, $R_3$, $R_7$, P, X, R, R', R", R"' and the asterisk * are as defined above, b) separating the diastereoisomeric salts of formulae (VII) to (XI) formed in the medium, and c) releasing the optically active α-aminoacetal of formula (R)-(I) or (S)-(I).

2. A process according to claim 1, wherein the compound of formula (I) is in racemic form or in the form of mixtures of enantiomers, wherein $R_1$ and $R_2$, which may be identical or different, are a linear or branched $C_1$-$C_6$ alkyl group;

$R_3$ is a group selected from the group consisting of: a substituted or unsubstituted, linear or branched $C_1$-$C_6$ alkyl group; a substituted or unsubstituted monocyclic, bicyclic or tricyclic $C_6$-$C_{14}$ aryl group; a substituted or unsubstituted arylalkyl group wherein the aryl and alkyl groups are as defined above; a substituted or unsubstituted $C_3$-$C_{10}$ cycloalkyl group; and a substituted or unsubstituted cycloalkylalkyl group wherein the cycloalkyl and alkyl groups are as defined above.

3. A process according to claim 1 wherein a compound of formula (I), in racemic form or in the form of mixtures of enantiomers, is reacted with an optically active α-amino acid represented by general formula (II) or (III)

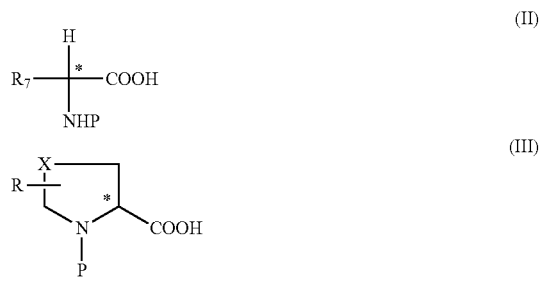

wherein $R_7$ is a linear or branched $C_1$-$C_6$ alkyl group which is unsubstituted or substituted with one or more hydroxyl, —NHP', —C(O)NH$_2$, —NH—C(=NH)—NHP', —SH, —S—CH$_3$, —CO$_2$H or phenyl groups, wherein P' is a hydrogen or an acetyl, propionyl, formyl, tosyl, benzoyl, ethoxycarbonyl, tert-butoxycarbonyl, benzyloxycarbonyl or 9-fluorenylmethoxycarbonyl group; a cyclohexyl group; a phenyl group; a benzyl or naphthyl group which is unsubstituted or substituted one or more times with a halogen atom, a hydroxyl group, an NO$_2$ group, a phenyl group or a $C_1$-$C_3$ alkoxy group; a pyridyl group; an imidazolylmethyl group; a pyridylmethyl group; or a thiazolylmethyl or indolylmethyl group;

P is an acetyl, propionyl, formyl, tosyl, benzoyl, ethoxycarbonyl, tert-butoxycarbonyl, benzyloxycarbonyl or 9-fluorenylmethoxycarbonyl group;

X is a carbon atom;

R is a hydrogen atom.

4. A process according to claim 1, wherein the optically active α-amino acid is selected from the group consisting of: N-acetyl-(L)-phenylalanine, N-acetyl-(D)-phenylalanine, N-acetyl-(L)-leucine, N-acetyl-(D)-leucine, N-acetyl-(L)-valine, N-acetyl-(D)-valine, N-acetyl-(L)-tyrosine, N-acetyl-(D)-tyrosine, N-acetyl-(L)-methionine, N-acetyl-(D)-methionine, N-acetyl-(L)-asparagine, N-acetyl-(D)-asparagine, N-tosyl-(L)-phenylalanine, N-tosyl-(D)-phenylalanine, N-ethoxy-carbonyl-(L)-phenylglycine and N-ethoxycarbonyl-(D)-phenylglycine.

5. A process according to claim 1, wherein the optically active α-amino acid is N-acetyl-(L)-phenylalanine or N-acetyl-(D)-phenylalanine.

6. A process according to claim 1, wherein a molar ratio of optically active α-amino acid of between 0.1 and 1 molar equivalent, relative to the compound of formula (I) is used.

7. A process according to claim 1, wherein the solvent is selected from the group consisting of isopropanol, ethanol, water, acetone, methyl isobutyl ketone, tetrahydrofuran, acetonitrile, ethyl acetate, toluene, methyl tert-butyl ether, and mixtures thereof.

8. A process according to claim 1, wherein the concentration of the compound of formula (I) in step a) is between 1% and 40% by weight.

9. A process according to claim 1, wherein the reaction temperature in step a) is between 0° C. and 120° C.

10. A process according to claim 1, wherein the separation in step b) is carried out by precipitation of the diastereoisomeric salt which is the least soluble of the diastereoisomeric salts formed in the reaction medium, and filtration of the precipitated diastereoisomeric salt from the reaction medium.

11. A process according to claim 1, wherein step c) is carried out by treatment of the separated diastereoisomeric salt with an alkaline or acidic aqueous solution.

12. A process according to claim 1, wherein before releasing the optically active α-aminoacetal of formula (R)-(I) or (S)-(I), as defined above, the diastereoisomeric salts of formulae (VII) to (XI) obtained after step b) are subjected to at least one recrystallization or reslurrying step.

13. A process according to claim 1, further comprising the steps of:
recovering, from the reaction medium, a diastereoisomeric salt according to general formulae (VI) to (XI), which was not separated during step b), and
releasing the optically active α-aminoacetal of formula (R)-(I) or (S)-(I).

14. A process according to claim 1, wherein a molar ratio of optically active α-amino acid of 0.5 molar equivalent, relative to the compound of formula (I) is used.

15. A process according to claim 1, wherein the concentration of the compound of formula (I) in step a) is between 3% and 9% by weight.

16. A process according to claim 1, wherein the reaction temperature in step a) is between 5° C. and the boiling point of the reaction medium.

17. A process according to claim 1, wherein separating the salts in step (b) comprises one or two recrystallizations and the optically active α-aminoacetal of formula (R)-(I) or (S)-(I) product released in step (c) has an optical purity of greater than 95%.

18. A process according to claim 17, wherein separating the salts in step (b) comprises only one recrystallization.

19. A process according to claim 17, wherein recrystallization of the salts in step (b) is carried out at a temperature between 0° C. and 120° C.

20. A process according to claim 17, wherein the optically active α-aminoacetal is released from the corresponding diastereomeric salt by treatment of the salt with a base.

\* \* \* \* \*